United States Patent [19]

Kodama et al.

[11] Patent Number: 4,729,955

[45] Date of Patent: Mar. 8, 1988

[54] METHOD OF PRODUCING REVERSE TRANSCRIPTASE

[75] Inventors: Michi Kodama; Kiichi Sekiguchi, both of Ibaraki; Masanori Kubo, Kagoshima, all of Japan

[73] Assignee: Director of The National Institute of Animal Health, Ibaraki, Japan

[21] Appl. No.: 559,383

[22] Filed: Dec. 8, 1983

[30] Foreign Application Priority Data

Dec. 23, 1982 [JP] Japan ................................. 57-224947

[51] Int. Cl.$^4$ ......................... C12N 9/00; C12N 5/00; C12R 1/91
[52] U.S. Cl. ................................. 435/183; 435/240.2; 435/948
[58] Field of Search ............... 435/183, 240, 241, 235, 435/42, 43, 240.2, 948

[56] References Cited

FOREIGN PATENT DOCUMENTS 0126785  7/1983  Japan ................................. 435/948

OTHER PUBLICATIONS

Hizi et al., "RNA-Dependent DNA Polymerase of Avian Sarcoma Virus B77", *J. Biol. Chem.* 252(7), Apr. 10, 1977, pp. 2281-2289.

Strandstrom et al., "C-Type Particles Produced by a Permanent Cell Line from a Leukemic Pig", *Virology* 57, pp. 175-178 (1974).

Moennig et al., "C-Type Particles Produced by a Permanent Cell Line from a Leukemic Pig", *Virology* 57, pp. 179-188 (1974).

Reid et al., "New Techniques for Culturing Differentiated Cells: Reconstituted Basement Membrane Rafts", *Meth. Enzymology* LVIII, pp. 263-278 (1979).

Luben et al., "In vitro Immunization as an Adjunct to the Production of Hybridomas Producing Antibodies Against Lymphokine Osteoblast Activating Factor", *Molec. Imm.*, vol. 17, pp. 635-639, 1980.

Mizutani et al., "Endogenous RNA-Directed DNA Polymerase Activity in Virons of RNA Tumor Viruses and in a Fraction from Normal Chicken Cells", *Meth. Enzym.* XXIX, pp. 119-124, (1974).

Marcus et al., "Purification of Avian Myeloblastosis Virus DNA Polymerase by Affinity Chromatography on Polycytidylate Agarose", *J. Virol.*, vol. 14(1), pp. 853-859 (1974).

Lieber et al., "Biologic and Immunogenic Properties of Porcinae Type C Virus", *Virology* 66, pp. 616-619, (1975).

Lieber et al., 'Mammalian Cells in Culture Frequently Release Type C Viruses', *Science*, vol. 182, (1973), pp. 56-59.

Beneviste et al., 'Multiple Divergent Copies of Endogenous C-Type Virogenes in Mammalian Cells'; *Nature*, vol. 252, (1974), pp. 170-173.

Weiss, R. et al., editors, *RNA Tumor Viruses*, 2d ed., publ. Cold Spring Harbor Labortory, Cold Spring Harbor, New York; 1982, pp. 120, 121, 378 and 381.

*Primary Examiner*—Elizabeth Weimar
*Attorney, Agent, or Firm*—Frishauf, Holtz, Goodman & Woodward

[57] ABSTRACT

A method of producing reverse transcriptase, which comprises isolating a fraction containing retrovirus from a tissue culture fluid supernatant of retrovirus producing cells which are able to grow and propagate in vitro, treating said fraction at least once by sucrose density gradient centrifugation to thereby obtain a purified retrovirus, and extracting reverse transcriptase from said purified retrovirus.

14 Claims, 6 Drawing Figures

METHOD OF PRODUCING REVERSE TRANSCRIPTASE

BACKGROUND OF THE INVENTION

Reverse transcriptase is a DNA(RNA-DNA hybrid)-synthesizing enzyme using RNA as a template, which was discovered in Rausher murine leukemia virus (R-MLV) by Baltimore, 1970, and in Raus sarcoma virus (RSV) by Temin and Mizutani. This enzyme has been demonstrated in virions of RNA-containing tumor viruses and functions to make DNA complements of the RNA genoms. The resulting DNA, as a provirus, is integrated into the host cell chromosome and induces virus multiplication and transformation.

With the latest development of recombinant DNA techniques, reverse transcriptase has been widely used for synthesizing the complementary DNA (cDNA) from RNA and the demand for this enzyme has increased remarkably.

Reverse transcriptase has been produced using the plasma of chicks inoculated with avian myeloblastosis virus (AMV). However, this method requires the selection and conservation of chicken lines highly sensitive to AMV, as well as the use of special facilities and techniques for sampling at an appropriate stage of the disease. Because this method is complex, costly and time consuming, there has developed a need to establish simplified procedures to obtain reverse transcriptase, such as a method of using culture cells.

Purification of reverse transcriptase has been attempted by using culture cells of avian retrovirus as well as of mammalian retrovirus such as that obtained from the mouse and the monkey. However, these purification procedures require a large amount of materials for obtaining a suitable amount of the viruses, as well as a great deal of work and time for the treatment of these materials. Culture cells of mammalian retrovirus have not yet been successfully employed to produce the enzyme having a high specific activity.

It is therefore an object of the present invention to provide a cell line which can be cultured, propagated and transferred to produce retroviruses from which reverse transcriptase may be obtained.

It is a further object of the invention to extract the reverse transcriptase from the retroviruses and to subsequently purify the reverse transcriptase.

SUMMARY OF THE INVENTION

The present invention relates to a method for the production of reverse transcriptase. More particularly, the present invention relates to a method of isolating retrovirus from the culture fluid of retrovirus producing cells, and extracting the reverse transcriptase from the retrovirus, followed by purification of the thus obtained reverse transcriptase.

DETAILED DESCRIPTION OF THE INVENTION

Figure 1:
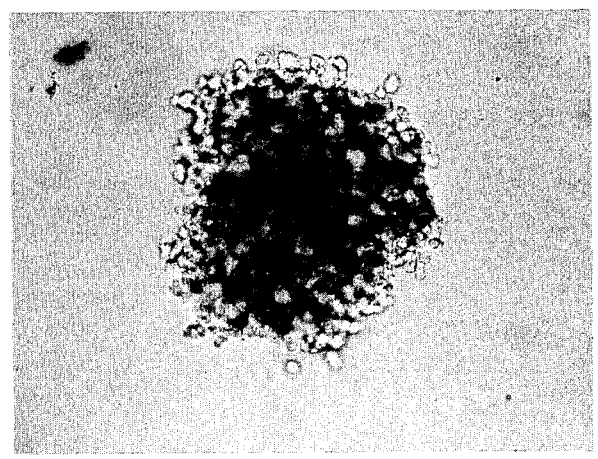
FIG. 1 is a photograph of colonies examined on the 20th day of planting porcine tumor cells on 0.3% soft agar.

The present inventors have discovered that a tumor infected mammalian organ preferably the spleen of a leukemic pig produces a tumor cell line (Shimozuma cells) which is capable of releasing a large amount of C-type particles (i.e., retrovirus) from which reverse transcriptase having high specific activity may be obtained in a simplified manner. Further, this tumor cell line is easy to maintain.

The method of producing reverse transcriptase according to the present invention comprises isolating a fraction containing retrovirus from a tissue culture fluid supernatant of retrovirus producing cells which are able to grow and propagate in vitro, purifying the fraction thus obtained by sucrose density gradient centrifugation, and extracting reverse transcriptase from the purified retrovirus.

Retrovirus producing cells, especially porcine retrovirus producing cells which can be cultured in vitro can be obtained from tumor cells of a suitably infected pig organ. The tumor cells are removed, suspended and cultured. The cultured tumor cells are co-cultured in the presence of a suitable nutrient source such as thymus cells. Then, the co-cultured cells are cultured in the presence of a suitable medium. The thus obtained co-cultured cells are subjected to a well-known soft agar cloning method (G. Köhler and C. Milstein, Eur. J. Immunol, 6, 511 (1976), R. H. Kennett, Monoclonal Antibodies (ed. R. H. Kennett et al.) p 372 Plenum (1980)) to thereby maximize the population of tumor cells containing a high quality of retrovirus.

The present process requires the isolation of a fraction containing retrovirus from a tissue culture fluid supernatant of the retrovirus cells. The culture fluid is centrifuged to obtain the supernatant and then the supernatant is concentrated to obtain a solid product containing the retrovirus.

The solid product is then dissolved in a buffered solution and the buffered solution is subjected to at least one density gradient centrifugation treatment in the presence of sucrose to thereby obtain a purified retrovirus.

The purified retrovirus is dissolved in a buffered solution containing the detergent, sonicated and the resulting sonicated solution is subjected to column chromatography or centrifugation to thereby obtain a fraction containing reverse transcriptase. In a preferred form of the invention, several different types of chromatographic column may be used to obtain a fraction containing substantially pure reverse transcriptase. Alternatively, centrifugation may be used to obtain substantially pure reverse transcriptase.

The following Examples are for illustrative purposes only and are not meant to limit the invention set forth in the claims appended hereto.

EXAMPLE 1

An enlarged (tumor)spleen of a pig infected with spontaneous leukemia, was minced, sieved and washed by centrifugation. The thus obtained tumor cells were suspended at a concentration of $8.5 \times 10^6$ cells/ml in RPMI-1640 medium (Difco laboratories) containing 10% bovine serum and statically cultured in a $CO_2$ incubator for 4 days.

The cultured tumor cells were added to thymus cells of a healthy piglet, and co-cultured for 32 days.

The resulting co-cultured cells were successively transfer-cultured at intervals of 3 days, and on the 60th day the co-cultured cells were subjected to a soft agar cloning method to thereby obtain a tumor cell line (The Shimozuma cell).

The tumor cells of the tumor cell line have the following characteristics:

(1) When planted at a concentration of 10,000 cells/ml, the cells grow, propagate and are able to be successively transfer-cultured. The cell population doubles in 13 hours, and the maximum cell density is $20-40 \times 10^4$ cells/cm$^2$;

(2) As shown in FIG. 1, colonies are formed by the 20th day of planting on 0.3% soft agar;

(3) Rosette is not formed by sheep red blood cells;

(4) The chromosome number is in a range of 53 to 71; and (5) A large quantity of retrovirus is spontaneously released.

Thus, the tumor cells are extremely suitable materials for obtaining reverse transcriptase.

EXAMPLE 2

Retrovirus is obtained from the culture fluid supernatant of the tumor cells prepared in accordance with Example 1. The retrovirus is then purified and solubilized to prepare reverse transcriptase.

The tumor cells prepared in accordance with Example 1 were cultured while being rotated in a roller bottle at 37°±2° C. Every 6 to 16 hours, the culture fluids were harvested and centrifuged by a low-speed centrifuge operating at from 3000 to 5000 rpm for 5 to 10 minutes to obtain a supernatant and to separate the cells therefrom.

Alternatively, the retrovirus producing cells may be cultivated in an Eagle's minimum essential medium containing 5 to 10% bovine serum and 0.07 to 0.14% sodium bicarbonate.

The supernatant was concentrated to $\frac{1}{3}$ to $\frac{1}{4}$ of the original volume by AG gum (Dai-ichi Kogyo Seiyaku Co., Ltd.) and the concentrate was placed into a centrifuge tube on 10 to 20% glycerine in a TNE buffer solution (0.01M Tris-HCl pH 7.4, 0.1N NaCl, 1 mM EDTA), and centrifuged at about 23,000 to 27,000 rpm, preferably about 25,000 rpm for between 110 and 80 minutes, preferably about 90 minutes to thereby obtain pellets. The pellets were suspended in a TNE buffer solution and then subjected to density gradient centrifugation in 15 to 60% (w/v) sucrose at about 16,000 to 20,000 rpm, preferably about 18,000 rpm for about 20 to 13 hours, preferably about 16 hours to thereby collect the fractions having a density of 1.15–1.16 g/ml. The thus collected fractions were concentrated by centrifugation at about 35,000 to 45,000 rpm, preferably about 40,000 rpm for about 80 to 40 minutes, preferably about 60 minutes and again subjected to sucrose density gradient centrifugation at about 16,000 to 20,000 rpm, preferably about 18,000 rpm for about 20 to 13 hours, preferably about 16 hours to obtain purified retrovirus. The purified retrovirus was thus obtained at a ratio of 4 to 5 milligrams protein/1 liter cell fluid.

The purified retrovirus was then solubilized by adding the purified retrovirus to a solution containing 0.5% Nonidet P-40 (NP-40) (Shell Chemical Co.), 0.04M Tris-HCl (pH 8.0), 0.15M NaCl, 2 mM dithiothreitol, 20% glycerol and 1 mM EDTA. The solution was then sonicated and allowed to stand at 4° C. for about 1 hour to thereby produce the solubilized retrovirus.

EXAMPLE 3

Figure 2:
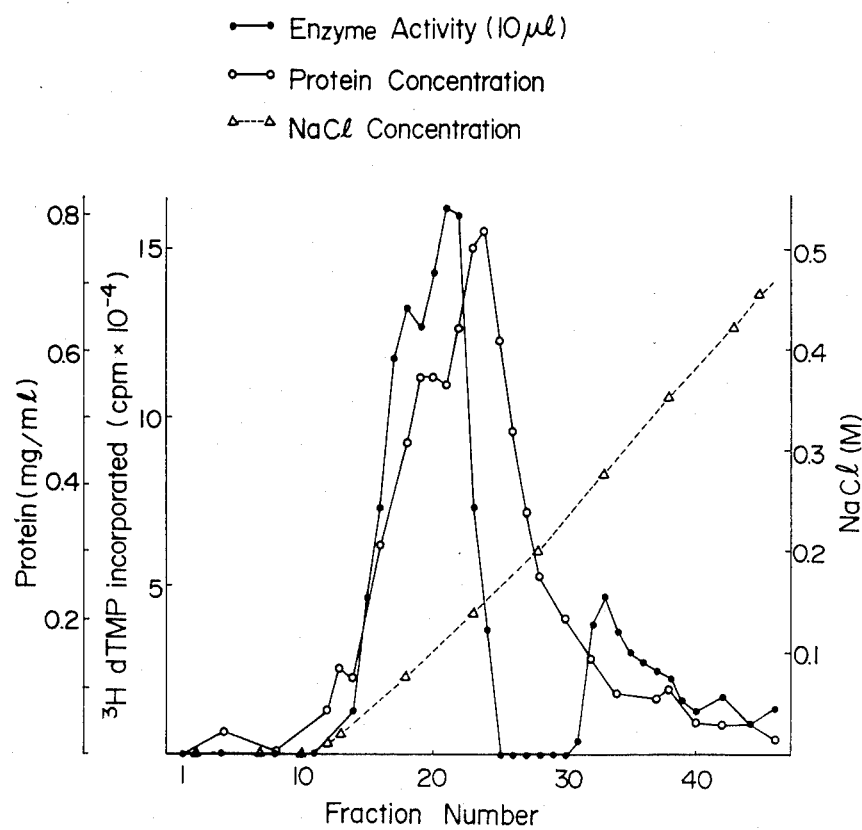
FIG. 2 is a graph of a DEAE-cellulose chromatograph of reverse transcriptase.

Reverse transcriptase can be prepared from the solubilized retrovirus, for example, by employing at least one chromatographic method using DEAE-cellulose, phosphocellulose, CM-cellulose, poly C agarose, poly U agarose and Sephadex G-100; and/or cesium chloride step gradient centrifugation and glycerol gradient centrifugation. In this Example, however, the preparation of reverse transcriptase from solubilized retrovirus was carried out according to the method of Hizi & Joklik (A. Hizi and W. K. Joklik: RNA-dependent DNA polymerase of Avian sarcoma virus; J. Biol. Chem. 252, 2281–2289 (1977)) and Marcus et al. (S. L. Marcus, M. J. Modak and L. F. Cavalieri; Purification of Avian myeloblastosis virus DNA polymerase by affinity chromatography on polycytidylate-agarose, J. Virol. 14, 853–859 (1974) modified as follows:

The solubilized retrovirus was dialyzed against a DEAE-cellulose buffer solution (0.02M Tris-HCl pH 7.5, 0.2% NP-40, 20% glycerol, 1 mM dithiothreitol) which was then loaded onto a DEAE-cellulose column which was eluted with a linear gradient of 0.02 to 0.7M NaCl. As shown in FIG. 2 (solid line) the reverse transcriptase activity was eluted at from 0.1 to 0.15M NaCl.

Figure 3:
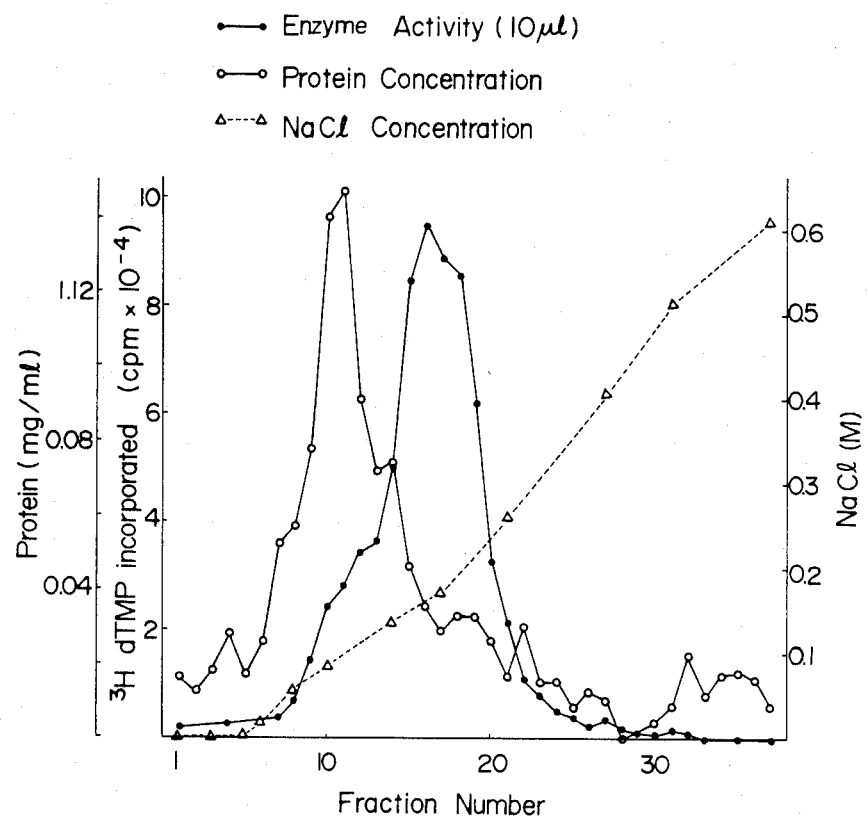
FIG. 3 is a graph of a phosphocellulose chromatograph of reverse transcriptase.

The reverse transcriptase active fractions were collected and dialyzed against a phosphocellulose buffer solution (0.05M Tris-HCl pH 8.0, 0.2% NP-40, 20% glycerol, 1 mM dithiothreitol) and loaded onto a phosphocellulose column which was eluted with a linear gradient of 0.05 to 0.8M NaCl. As shown in FIG. 3 (solid line), the peak of reverse transcriptase activity was detected in the eluates at from 0.2 to 0.28M NaCl.

Figure 5:
FIG. 5 is a photograph of poly C agarose purified reverse transcriptase by SDS polyacrylamide gel electrophoresis.
Figure 4:
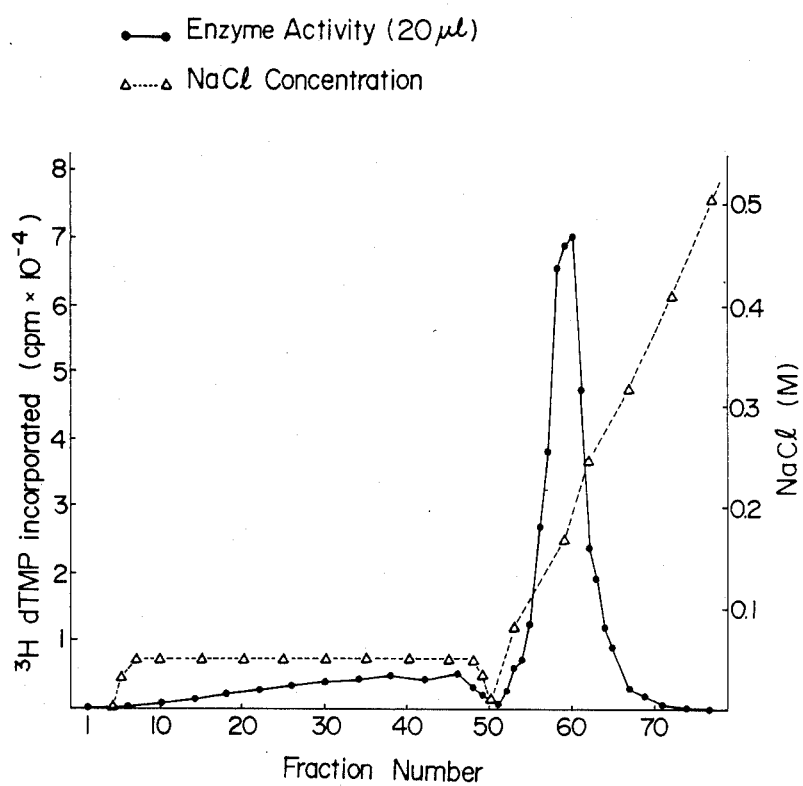
FIG. 4 is a graph of a poly C agarose chromatograph of reverse transcriptase.

The combined active fractions were diluted 6 fold with a phosphocellulose buffer solution and loaded onto a poly-C agarose column which was washed with a phosphocellulose buffer solution and then eluted with a linear gradient of 0.05 to 0.6M NaCl. As shown in FIG. 4, the reverse transcriptase active fractions were eluted at about 0.2M NaCl. Analysis of the active fractions by SDS-polyacrylamide gel electrophoresis (FIG. 5) showed that the active fractions are composed of components having a molecular weight of about 70,000 and 80,000 respectively.

Figure 6:
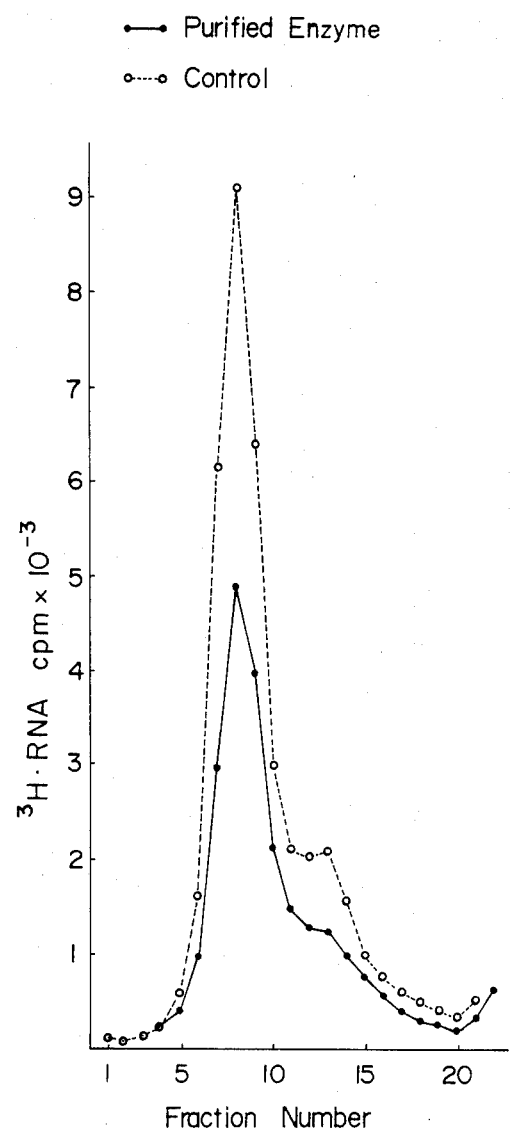
FIG. 6 is a graph of an assay for ribonuclease activity in poly C agarose purified reverse transcriptase.

The active fractions were tested in the following manner to detect for ribonuclease contamination. The active fractions were incubated with a $^3$H-labeled 28 S fraction of ribosome RNA of cells at 37° C. for 1 hour, which were then subjected to density gradient centrifugation in 15 to 30% (w/v) sucrose at 40,000 rpm for 5 hours. As shown in FIG. 6 (solid line), the centrifugation pattern was almost the same as that of the control (dotted line) consisting only of a buffer solution (containing no enzyme). The test showed that the active fractions were not contaminated with ribonuclease.

The reverse transcriptase was then assayed according to the method of Hizi & Joklik (A. Hizi and W. K. Joklik: RNA-dependent DNA polymerase of Avian sarcoma virus; J. Biol. Chem. 252, 2281–2289 (1977) using the template, poly(rA)n(dT)$_{12-18}$.

0.1 ml of a reaction solution containing 0.05M Tris buffer solution (pH 8.0), 0.06M NaCl, 0.1 mM $MnCl_2$, 5 mM dithiothreitol and 50 μM $^3$H-dTTP (thymidine triphosphate; specific activity: 123 cpm/p mole) was incubated at 37° C. for 1 hour and loaded onto DE 81 filter paper discs which were washed 6 times with 5% Na$_2$HPO$_4$ every 10 minutes and twice with water and ethanol. The filter paper discs were dried and counted in a toluene-based scintillator. In this assay, one unit of reverse transcriptase activity was defined as the amount of enzyme which incorporates 1 nanomole of $^3$H-dTMP into the acid insoluble material in 1 minute.

Table 1 shows the reverse transcriptase activity of the intermediate products obtained during the course of the purification procedures described previously:

TABLE 1

|  | Reverse Transcriptase Activity (unit) | Protein (mg) | Specific Activity (U/mg) |
|---|---|---|---|
| solubilized retrovirus | 95.0 | 54.4 | 1.74 |
| DEAE-cellulose fraction | 26.2 | 7.00 | 3.74 |
| Phosphocellulose fraction | 25.1 | 0.996 | 25.2 |
| Poly C agarose fraction | 6.23 | 0.041 | 150 |

The results of Table 1 show that the specific activity of the reverse transcriptase of the resulting intermediate products increases over the course of the purification procedures.

The method according to the present Examples results in the production of high potency reverse transcriptase in a high yield from porcine tumor cells in a simplified manner.

What is claimed is:

1. A method of producing reverse transcriptase, which comprises isolating a fraction containing retrovirus from a tissue culture fluid supernatant of retrovirus producing cells, said retrovirus producing cells being Shimozuma cells IFO 50136; said retrovirus producing cells being grown and propagated in vitro, treating said fraction at least once by sucrose density gradient centrifugation to thereby obtain a purified retrovirus, and extracting and isolating reverse transcriptase from said purified retrovirus.

2. The method according to claim 1, wherein the retrovirus producing cells are cultivated in an Eagle's minimum essential medium containing from 5 to 10 percent of bovine serum and from 0.07 to 0.14 percent of sodium bicarbonate.

3. The method according to claim 1, wherein the retrovirus producing cells are cultivated by a rotating-culture method at 37 ±2° C. for 6 to 16 hours to thereby obtain a culture fluid.

4. The method according to claim 1, wherein the culture fluid of the retrovirus producing cells is centrifuged to obtain a supernatant of said culture fluid containing said retrovirus.

5. The method of claim 4, wherein the step of centrifuging said culture fluid is conducted at the rate of 3,000 to 5,000 rpm for between 5 and 10 minutes.

6. The method of claim 4 further comprising:
concentrating the supernatant to obtain a solid product containing said retrovirus, forming a buffered solution containing said solid product, and subjecting said buffered solution to density gradient centrifugation in the presence of sucrose at least once to thereby obtain a purified retrovirus.

7. The method of claim 6, wherein the step of concentrating the supernatant further comprises:
(a) reducing the volume of the supernatant to between ⅛ and ¼ of the original volume to form a concentrate;
(b) subjecting said concentrate to centrifugation for a time sufficient to form pellets containing said retrovirus.

8. The method of claim 7, wherein said centrifugation is conducted at a rate of between 23,000 and 27,000 rpm for between 110 and 80 minutes respectively.

9. The method of claim 8, wherein said centrifugation is conducted at about 25,000 rpm for about 90 minutes.

10. The method of claim 6, wherein the buffered solution containing said solid product is subjected to density gradient centrifugation at a rate of 16,000 to 20,000 rpm for 20 to 13 hours respectively in the presence of sucrose having a concentration of 15 to 60% w/v.

11. The method of claim 10, wherein said density gradient centrifugation is conducted at a rate of about 18,000 rpm for about 16 hours.

12. The method of claim 1, wherein the step of extracting reverse transcriptase from said purified retrovirus further comprises:
dissolving said purified retrovirus in a buffered solution, sonicating said buffered solution containing detergent, and subjecting said sonicated solution to column chromatography or centrifugation to thereby obtain a first fraction containing reverse transcriptase.

13. The method of claim 12 further comprising dialyzing said sonicated solution against a DEAE-cellulose buffered solution, loading said buffered solution onto a column of DEAE-cellulose and eluting the buffered solution with a linear gradient of from 0.02 to 0.7M NaCl, whereby a first fraction containing reverse transcriptase is eluted at from 0.1 to 0.15M NaCl.

14. The method of claim 13 further comprising dialyzing the first fraction against a phosphocellulose buffered solution, loading said buffered solution onto a column of phosphocellulose, and eluting the buffered solution with a linear gradient of from 0.05 to 0.8M NaCl to thereby collect a fraction containing reverse transcriptase, said fraction being eluted at from 0.2 to 0.28M NaCl, diluting said fraction with a phosphocellulose buffered solution, loading said buffered solution onto a column of poly-C agarose, and eluting the buffered solution with a linear gradient of from 0.05 to 0.6M NaCl, to thereby obtain a substantially pure fraction of reverse transcriptase, said substantially pure fraction being eluted at 0.2M NaCl.

* * * * *

UNITED STATES PATENT AND TRADEMARK OFFICE
CERTIFICATE OF CORRECTION

PATENT NO. : 4,729,955

DATED : March 8, 1988

INVENTOR(S) : KODAMA et al

It is certified that error appears in the above-identified patent and that said Letters Patent is hereby corrected as shown below:

Column 6, lines 32-33 (Claim 12): Rewrite as follows:

--tion containing detergent, sonicating said buffered solution, and subjecting said sonicated solution to--

Signed and Sealed this

Twenty-ninth Day of December, 1992

*Attest:*

DOUGLAS B. COMER

*Attesting Officer*   Acting Commissioner of Patents and Trademarks